United States Patent
Sato

(10) Patent No.: US 6,175,612 B1
(45) Date of Patent: Jan. 16, 2001

(54) IN-LINE FLUORESCENT X-RAY FILM THICKNESS MONITOR

(75) Inventor: Masao Sato, Chiba (JP)

(73) Assignee: Seiko Instruments Inc. (JP)

( * ) Notice: Under 35 U.S.C. 154(b), the term of this patent shall be extended for 0 days.

(21) Appl. No.: 09/243,919

(22) Filed: Feb. 3, 1999

(30) Foreign Application Priority Data

Feb. 3, 1998 (JP) .................................. 10-022250

(51) Int. Cl.⁷ .................................................. G01N 23/223
(52) U.S. Cl. ............................ 378/50; 378/121; 313/358; 250/370.06
(58) Field of Search ............................. 378/50, 121, 119; 313/358; 250/370.06

(56) References Cited

U.S. PATENT DOCUMENTS 3,895,250 * 7/1975 Christgau et al. .................... 313/358
5,113,421 * 5/1992 Gignoux et al. ........................ 378/50
5,574,284 * 11/1996 Farr .................................. 250/370.06

* cited by examiner

*Primary Examiner*—David P. Porta
*Assistant Examiner*—Pamela R. Hobden
(74) *Attorney, Agent, or Firm*—Adams & Wilks

(57) ABSTRACT

In order to improve detection efficiency and angular detection characteristics of an in-line X-ray film thickness monitor for monitoring the film thickness of a coated part during production of a product formed using the coated part, the film thickness monitor is provided with an X-ray tube of an end-window type for irradiating an X-ray beam onto the coated part, and an X-ray detector having an annular detecting plane arranged coaxially with the axis of irradiation of the X-ray beam. The X-ray detector detects fluorescent X-rays emitted by the coated part in response to irradiation thereof by the X-ray beam so that the thickness of the coating film can be determined based upon the intensity of the detected fluorescent X-rays.

9 Claims, 2 Drawing Sheets

FIG. 2A PRIOR ART    FIG. 2B
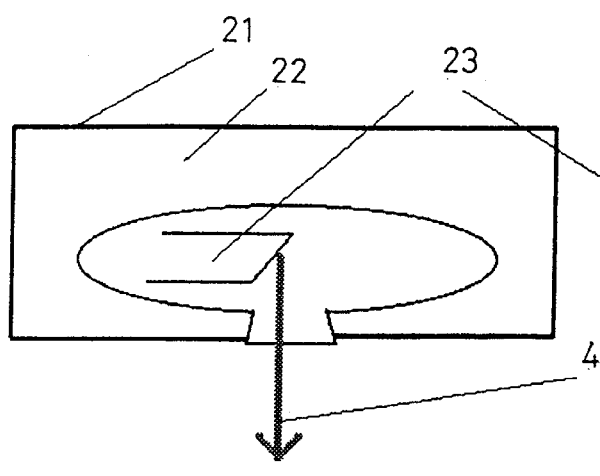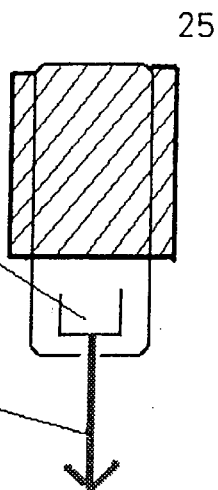
FIG. 3A PRIOR ART    FIG. 3B
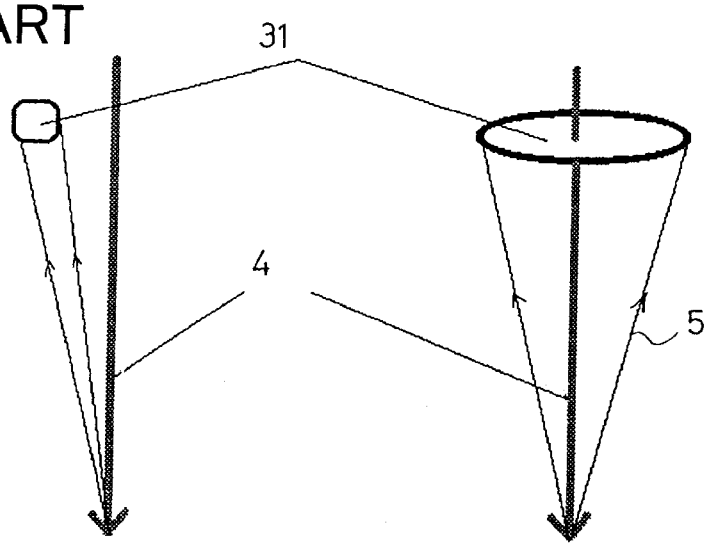

IN-LINE FLUORESCENT X-RAY FILM THICKNESS MONITOR

BACKGROUND OF THE INVENTION

The present invention relates to a small-sized fluorescent X-ray film thickness monitor to be installed in a manufacturing line in order to monitor for nickel electroless plating film thickness on aluminum substrate of a hard disc.

As hard disc density increases, there is a growing problem of base flatness or evenness in opposite surface film thickness of substrate electroless nickel plating. It is becoming important to monitor electroless nickel plating film thickness immediately after electroless nickel plating or before or after polishing in a manufacturing line. Conventionally, sampling inspections have been conducted with an off-line fluorescent X-ray gauge.

The conventional sampling inspection has involved a problem in that occurrence of a product rejection results in a rejection on a lot basis thus raising a rejection rate under recent severe criteria. Due to this, there has been a necessity to adjust working conditions to decrease the rate of rejection by conducting an in-line re-measurement for immediate feedback. In installing a fluorescent X-ray film thickness gauge in the production line of a coated part, there has been a dimensional problem of an X-ray generating system as well as a problem of fluttering of measurement samples. Therefore, it is an object of the present invention to provide a fluorescent X-ray monitor that is small in size and excellent in characteristic for in-line installation in the production line of a coated part for measuring the film thickness of the coating applied to the part.

SUMMARY OF THE INVENTION

In a conventional monitor, an X-ray tube 23 of a side window-type, which is shown in FIG. 2A, is immersed in an insulation oil 22 disposed in an oil tank 21 for discharge prevention and cooling purposes due to the use of high pressure. Accordingly, it has been impossible to decrease the size and to reduce the weight of the conventional monitor. In respect of this problem, by employing an end window-type X-ray tube having a casing 25 molded by silicone resin or the like for irradiating a coated part with a collimated X-ray beam, as shown in FIG. 2B, it is possible to decrease the size and reduce the weight of the monitor and to further place an X-ray generation point in a production line close to the sample as compared with the X-ray tube of the side window-type, thereby also improving the excitation efficiency.

In respect of fluttering in measurement samples, although a conventional monitor has conducted detection by placing a detector 31 for detecting electromagnetic waves irradiated by the sample in response to irradiation by the X-ray at a certain angle with respect to a primary X-ray irradiation axis 4, as shown in FIG. 3A, and hence had an angular characteristic, it is possible to solve the fluttering problem by arranging an annular detector 31 coaxial to the irradiation axis 4 as shown in FIG. 3B.

Also, because the annular type detector can afford to have a great solid angle and hence improve efficiency, it is possible to decrease an affection difference of an inverse square law on distance caused by increasing an irradiation-detection distance, i.e., a distance from a detection plane to a sample, and also to improve the distance characteristic.

BRIEF DESCRIPTION OF THE DRAWINGS

FIG. 2A is a side window-type X-ray tube, and

FIG. 2B is an end window-type X-ray tube; and

FIGS. 3A and 3B are illustrative views showing an arrangement of an X-ray detector.

DETAILED DESCRIPTION OF THE PREFERRED EMBODIMENT

Figure 1:
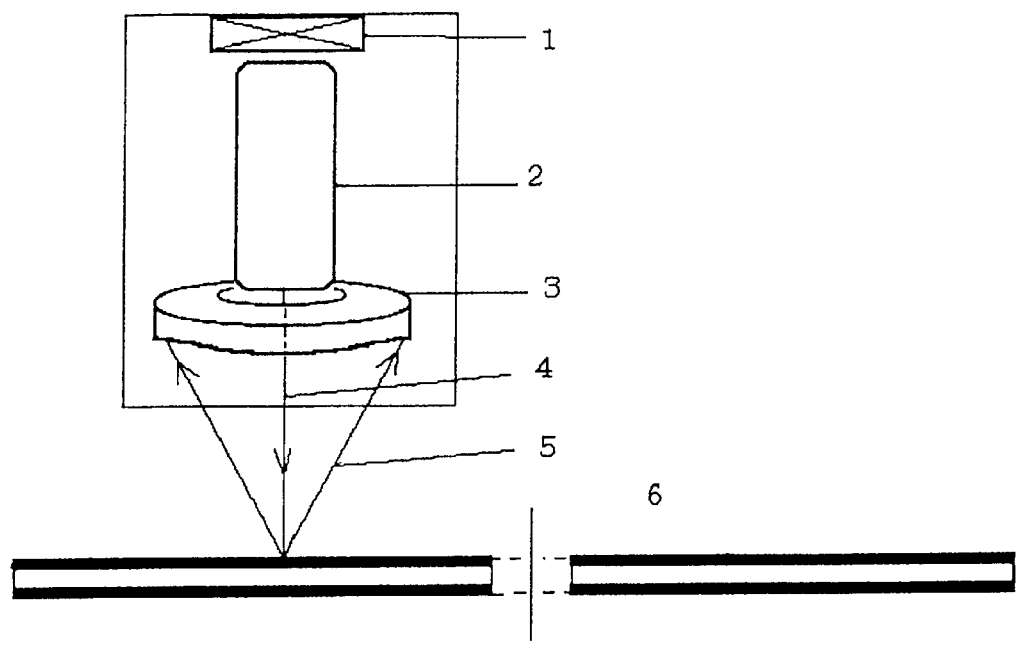
FIG. 1 is an embodiment of the present invention.

An embodiment of the X-ray film thickness monitor according to the present invention is shown in FIG. 1. A hard disc measuring plane is preferably distant from an X-ray sensor 3 for a purpose of facilitating the handling of a hard disc 6 in order to measure electroless nickel plating film thickness on main and back surfaces of the hard disc 6. In such a sense, an arrangement as in the embodiment of FIG. 1 is preferred which can shorten a distance to a sample by use of X-ray generating means comprising an end window-type X-ray tube 2 on an X-ray generating side and, conversely, which can increase a distance on a detection side by securing a solid angle using an annular type X-ray detector 3.

A primary X-ray 4 is irradiated by being collimated from an end window-type X-ray tube 2 into a predetermined irradiation dimension and passed through a central portion of the annular type detector 3. An intensity or a fluorescent X-ray (Ni-K$\alpha$) 5, that is proportional to a film thickness of an electroless nickel plating made on a disc, i.e., aluminum, is measured by an annular type x-ray detector 3. The annular type X-ray detector 3 can employ a semiconductor detector utilizing Si or a scintillation counter utilizing a scintillator such as NaI.

The end window type X-ray tube 2 molded by a silicone resin is cooled with a cooling fan 1 arranged at rear end thereof opposite the X-ray projection end because it generates heat on the order of several tens of watts.

By the arrangement described above, the size can be reduced to or smaller than half as compared with the conventional structure. Because favorable performances are obtained for production line characteristics such as an angle characteristic and a distance characteristic, in-line installation is possible where installation space is less, thus enabling accurate and prompt film thickness monitoring.

What is claimed is:

1. A small-sized fluorescent X-ray film thickness monitor, comprising: an end-window type X-ray tube having a pair of elongated sides and a pair of short sides smaller in length than the elongated sides for projecting a collimated X-ray beam from one of the short sides in a direction parallel to the elongated sides onto a sample coated with a film; and a detector having an annular detection plane coaxial to the collimated X-ray irradiation beam for detecting a fluorescent X-ray irradiated by the sample in response to irradiation of the sample by the collimated X-ray beam; wherein the collimated X-ray beam is projected through a central opening in the detector.

2. A small-sized fluorescent X-ray film thickness monitor according to claim 1; wherein the X-ray tube has a casing formed of a molded silicone resin.

3. A small-sized fluorescent X-ray film thickness monitor according to claim 1; wherein the detector comprises a semiconductor X-ray detector.

4. A small-sized fluorescent X-ray film thickness monitor according to claim 1; wherein the detector comprises a scintillation counter.

5. A film thickness monitor for in-line film thickness measurement of a coated part during production of a product using the part, comprising: an X-ray tube of an end-window type for producing an X-ray beam for projection onto the part, the X-ray tube being arranged in a production line of a product formed using the coated part; and a radiation detector for detecting electromagnetic waves irradiated by the part in response to irradiation by the X-ray beam for measuring a thickness of a coating applied to the part, the detector having an annular detecting plane arranged coaxially with an irradiation axis of the X-ray beam.

6. A film thickness monitor according to claim 5; wherein the X-ray tube has a casing formed of a molded silicone resin.

7. A film thickness monitor according to claim 5; wherein the radiation detector is an X-ray detector for detecting an intensity of fluorescent X-rays emitted by the part in response to irradiation of the part with the X-ray beam.

8. A film thickness monitor according to claim 7; wherein the radiation detector comprises a semiconductor X-ray detector.

9. A film thickness monitor according to claim 7; wherein the detector comprises a scintillation counter.

* * * * *